United States Patent [19]
Sauter et al.

[11] Patent Number: 6,060,493
[45] Date of Patent: May 9, 2000

[54] PHENYL BENZYL ETHERS, PROCESS FOR PRODUCING THEM AND THEIR USE AS PESTICIDE AND FUNGICIDE

[75] Inventors: Hubert Sauter, Mannheim; Wassilios Grammenos, Ludwigshafen; Bernd Müller, Frankenthal; Klaus Oberdorf, Heidelberg; Norbert Götz, Worms; Franz Röhl, Schifferstadt; Eberhard Ammermann, Heppenheim; Gisela Lorenz, Hambach; Siegfried Strathmann, Limburgerhof, all of Germany

[73] Assignee: BASF Aktiengesellschaft, Ludwigshafen, Germany

[21] Appl. No.: 09/051,789
[22] PCT Filed: Sep. 30, 1996
[86] PCT No.: PCT/EP96/04263
§ 371 Date: Apr. 20, 1998
§ 102(e) Date: Apr. 20, 1998
[87] PCT Pub. No.: WO97/14693
PCT Pub. Date: Apr. 24, 1997

[30] Foreign Application Priority Data

Oct. 19, 1995 [DE] Germany .................... 195 38 855

[51] Int. Cl.[7] .................... A01N 43/76; A01N 43/26; C07D 263/04; C07D 333/32
[52] U.S. Cl. .................... 514/374; 514/439; 514/440; 548/217; 549/60; 549/65; 549/66; 549/451
[58] Field of Search ............ 548/217; 549/60, 549/65, 66, 451, 454, 453, 455; 514/374, 440, 439

[56] References Cited

U.S. PATENT DOCUMENTS 5,145,980  9/1992  Wenderoth et al. .............. 560/35

FOREIGN PATENT DOCUMENTS 400 417  12/1990  European Pat. Off. .

OTHER PUBLICATIONS

Advances in Org. Chem. vol. 6, 1969 285–388.
Int. Jrl. Of Methods in Synthetic Org. Chem. 1981, 501–584.
Int. Jrl. Of methods in Synthetic Org. Chem. 1985, 203–205.
Syn. of Hemiacetals, Acetals, and Ketals 154–164 (1970).
Reactions of Organosulfur Compounds, 1978, 101–105.

*Primary Examiner*—Johann Richter
*Assistant Examiner*—Ebenezer Sackey
*Attorney, Agent, or Firm*—Keil & Weinkauf

[57] ABSTRACT

A compound of the general formula I

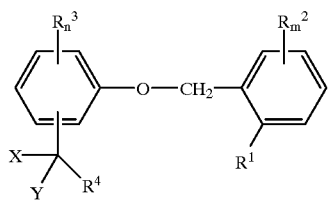

where the indices and the substituents have the following meanings:

$R^1$ is $C(CO_2CH_3)=CHOCH_3$, $C(CO_2CH_3)=NOCH_3$, $N(OCH_3)CO_2CH_3$ and $C(CONHCH_3)=NOCH_3$;
$R^2$ is cyano, halogen, $C_1-C_4$-alkyl and $C_1-C_4$-alkoxy;
m is 0 or 1;
$R^3$ is cyano, halogen, $C_1-C_4$-alkyl, $C_1-C_4$-haloalkyl and $C_1-C_4$-alkoxy;
n is 0, 1, 2 or 3, it being possible for the substituents $R^3$ to be different from each other when n is 2 or 3;
$R^4$ is hydrogen, $C_1-C_4$-alkyl, $C_1-C_4$-haloalkyl, $C_3-C_6$-cycloalkyl and phenyl;
X and Y are $C_1-C_6$-alkoxy, $C_1-C_6$-alkylthio, $C_1-C_6$-alkylamino, di-$C_1-C_6$-alkylamino or a $C_1-C_4$-alkylene chain which is bonded to the C atom directly or via an oxygen, sulfur and/or nitrogen atom and which can have attached to it one or two of the following substituents: oxo (=O), cyano, $C_1-C_4$-alkyl, $C_3-C_6$-cycloalkyl, $C_1-C_4$-alkoxycarbonyl, aryl and heteroaryl, their preparation and, their use.

6 Claims, No Drawings

PHENYL BENZYL ETHERS, PROCESS FOR PRODUCING THEM AND THEIR USE AS PESTICIDE AND FUNGICIDE

This application is a 371 PCT/EP 96/04263 filed on Sep. 30, 1996.

The present invention relates to compounds of the general formula I

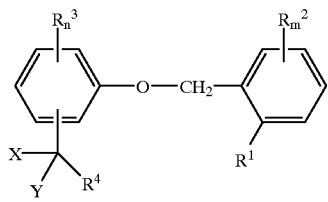

where the indices and the substituents have the following meanings:

$R^1$ is $C(CO_2CH_3)=CHOCH_3$, $C(CO_2CH_3)=NOCH_3$, $C(CONHCH_3)=NOCH_3$ and $N(OCH_3)-CO_2CH_3$;

$R^2$ is cyano, halogen, $C_1-C_4$-alkyl and $C_1-C_4$-alkoxy; m is 0 or 1;

$R^3$ is cyano, halogen, $C_1-C_4$-alkyl, $C_1-C_4$-haloalkyl and $C_1-C_4$-alkoxy;

n is 0, 1, 2 or 3, it being possible for the substituents $R^3$ to be different from each other when n is 2 or 3;

$R^4$ is hydrogen, $C_1-C_4$-alkyl, $C_1-C_4$-haloalkyl, $C_3-C_6$-cycloalkyl and phenyl;

X and Y are $C_1-C_6$-alkoxy, $C_1-C_6$-alkylthio, $C_1-C_6$-alkylamino, di-$C_1-C_6$-alkylamino or a $C_1-C_4$-alkylene chain which is bonded to the C atom directly or via an oxygen, sulfur and/or nitrogen atom and which can have attached to it one or two of the following substituents: oxo (=O), cyano, $C_1-C_4$-alkyl, $C_3-C_6$-cycloalkyl, $C_1-C_4$-alkoxycarbonyl, aryl and heteroaryl.

Furthermore, the invention relates to processes for the preparation of these compounds, to compositions comprising them, and to their use for controlling pests or harmful fungi.

Ketones or aldehydes of the phenyl benzyl ethers have been disclosed in the literature as intermediates (EP-A 513 580; DE-A 43 12 637).

It was an object of the present invention to provide novel active ingredients which have fungicidal and pesticidal properties.

We have found that this object is achieved by the compounds I defined at the outset. Furthermore, we have found processes for their preparation, compositions comprising them and their use for combating pests or harmful fungi.

The compounds I are prepared by methods similar to those disclosed in the literature.

For example, compounds I where the radicals X and Y together with the C atom to which they are bonded are an oxirane ring are obtained in a manner known per se [Reactions of Organosulfur Compounds, pp. 101–105, Academic Press, New York 1978; Adv. Org. Chem. 6, 285–388 (1969)] by reacting a carbonyl compound of the formula II with a trimethylsulfoxonium or trimethylsulfonium halide in an inert organic solvent in the presence of a base.

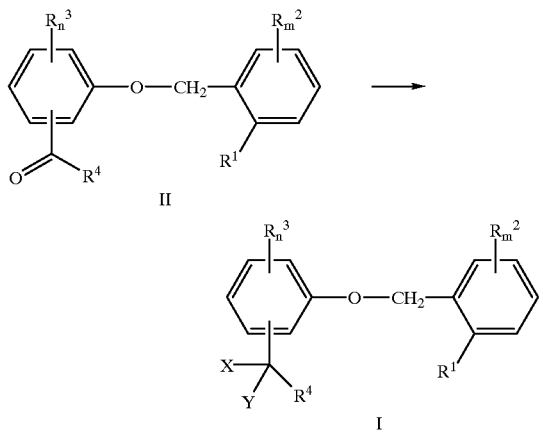

This reaction is usually carried out at from 0° C. to 150° C., preferably 20° C. to 120° C.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, and also dimethyl sulfoxide and dimethylformamide, particularly preferably dimethyl sulfoxide. mixtures of these can also be used.

Bases which are generally suitable are inorganic compounds such as alkali metal hydroxides and alkaline earth metal hydroxides, such as lithium hydroxide, sodium hydroxide, potassium hydroxide and calcium hydroxide, alkali metal hydrides and alkaline earth metal hydrides, such as lithium hydride, sodium hydride, potassium hydride and calcium hydride, organometallic compounds, especially alkali metal alkyls, such as methyllithium, butyllithium and phenyllithium, alkali metal alcoholates and alkaline earth metal alcoholates such as sodium methanolate, sodium ethanolate, potassium ethanolate, potassium tert-butanolate and dimethoxymagnesium. Sodium methoxide, sodium hydride, sodium hydroxide, potassium hydroxide and potassium tert-butoxide are particularly preferred.

The bases are generally employed in catalytic amounts, but can also be used in equimolar amounts, in an excess or, if suitable, as solvents.

The carbonyl compounds required for the preparation of the compounds I are described in the literature cited at the outset. Compounds I where the radicals X and Y are bonded to the C atom via an oxygen, sulfur or nitrogen atom and $R^1$ is $C[CONHCH_3]=NOCH_3$ are obtained, for example, by reacting a carbonyl compound of the formula II in a manner known per se [Synthesis 501–522 (1981), Synthesis 203 (1983); Carboxylic Ortho Ester Derivatives, pp. 154–164, Academic Press, New York 1970] in an inert organic solvent and optionally an acid and/or an acidic catalyst either a) with an alcohol, thiol and/or amine of the formula III or b) with a compound of the formula IV.

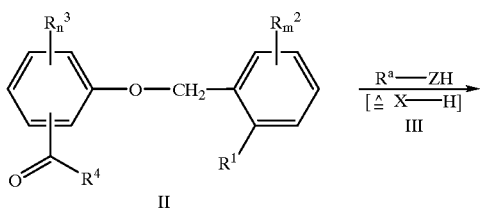

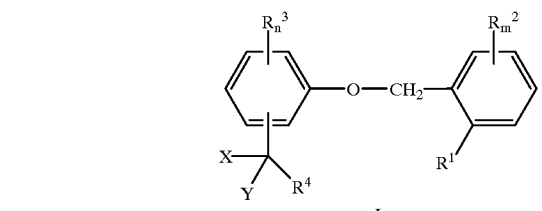

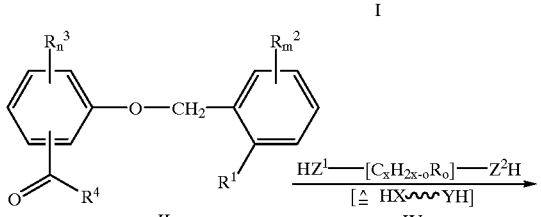

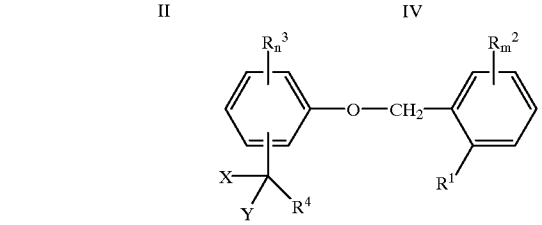

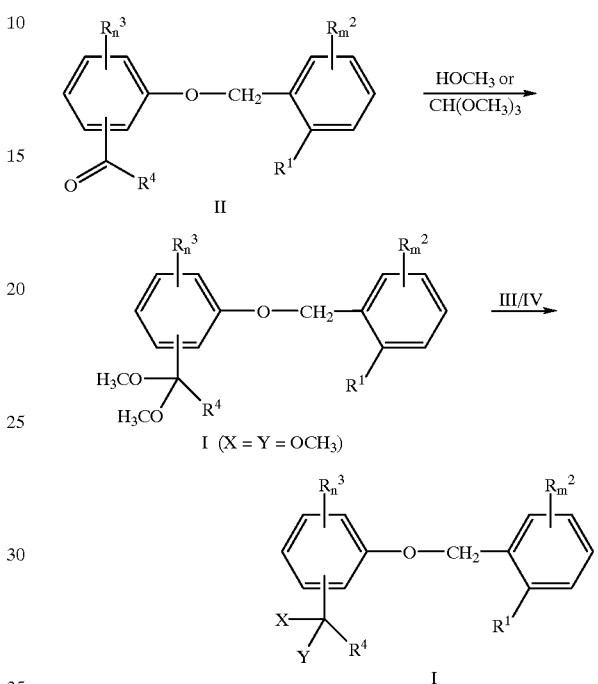

I (X = Y = OCH₃)

Compounds I where $R^a$ is not methyl are obtained particularly advantageously in a similar manner by first converting the carbonyl compound II with trimethyl formate or methanol to give the corresponding dimethyl acetal or dimethyl ketal (I, X=Y=OCH₃) and subsequently transacetalizing this product either with a compound III or with a compound IV.

In formula III, which generally represents compounds of the formulae XH and YH, $R^a$ is a $C_1$–$C_6$-alkyl group. Z in formula III are oxygen, sulfur, amino (NH) or $C_1$–$C_6$-alkylamino and $Z^1$ and $Z^2$ in formula IV are oxygen, sulfur or amino (NH).

Formula IV represents precursors where X and Y are a $C_1$–$C_4$-alkylene chain which is bonded to the C atom via oxygen, sulfur and/or nitrogen. Correspondingly, x is 1, 2, 3 or 4 and o is 0, 1, 2 or 3. R is $C_1$–$C_4$-alkyl, $C_3$–$C_6$-cycloalkyl, $C_1$–$C_4$-alkoxycarbonyl, cyano, aryl and heteroaryl or one or more CH₂ groups of the alkylene chain can be replaced by C=O.

This reaction is usually carried out at from 0° C. to 180° C., preferably 20° C. to 150° C.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, and dimethyl sulfoxide and dimethylformamide, particularly preferably toluene, methylene chloride, chlorobenzene and xylenes.

Mixtures of these can also be used.

Acids and acidic catalysts which may be used are inorganic acids such as hydrofluoric acid, hydrochloric acid, hydrobromic acid, sulfuric acid and perchloric acid, Lewis acids such as boron trifluoride, tin(IV) chloride, titanium (IV) chloride and zinc(II) chloride, and organic acids such as formic acid, acetic acid, propionic acid, oxalic acid, citric acid, trifluoroacetic acid, trifluoromethanesulfonic acid, methanesulfonic acid and toluenesulfonic acid.

The acids, or acidic catalysts, are generally used in catalytic amounts, but can also be used in equimolar amounts, in an excess or, if suitable as the solvent.

This reaction of II with trimethyl orthoformate is usually carried out at from 0° C. to 180° C., preferably 20° C. to 150° C.

Suitable solvents are aromatic hydrocarbons such as toluene, o-, m- and p-xylene, halogenated hydrocarbons such as methylene chloride, chloroform and chlorobenzene, and dimethyl sulfoxide and dimethylformamide, particularly preferably dimethyl sulfoxide and dimethylformamide. Mixtures of these can also be used.

Acids and acidic catalysts which may be used are inorganic acids such as hydrofluoric acid, hydrochloric acid, hydrobromic acid, sulfuric acid and perchloric acid, Lewis acids such as boron trifluoride, tin(IV) chloride and tin(II) chloride, and organic acids such as formic acid, acetic acid, propionic acid, oxalic acid, citric acid, trifluoroacetic acid, methanesulfonic acid and 4-methylphenylsulfonic acid.

The acids, or the acidic catalysts, are generally employed in catalytic amounts, but they can also be used in equimolar amounts, in an excess or, if suitable, as the solvent.

The educts are generally reacted with each other in equimolar amounts. It may be advantageous for the yield to employ trimethyl orthoformate in an excess or a substoichiometric amount, based on II.

In a further process, the compounds I are also obtained by reacting a phenol of the formula V with a benzyl compound of the formula VI in a manner known per se in an inert organic solvent in the presence of a base.

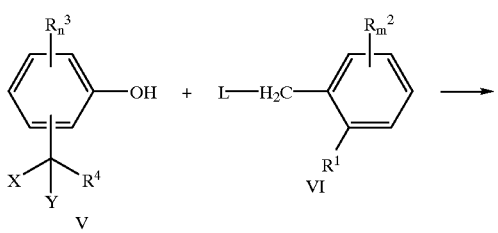

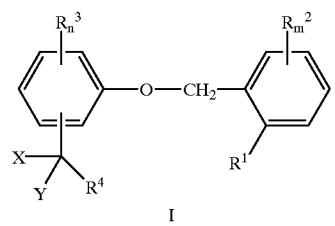

L in formula VI is a nucleophilically exchangeable group such as halogen (fluorine, chlorine, bromine and iodine, preferably chlorine, bromine and iodine) or an alkyl- or arylsulfonate group (eg. methylsulfonate, trifluoromethylsulfonate, phenylsulfonate and 4-methylphenylsulfonate).

This reaction is usually carried out at from 0° C. to 120° C., preferably 20° C. to 85° C.

Suitable solvents are ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and dimethyl sulfoxide and dimethylformamide, particularly preferably tetrahydrofuran, acetone, acetonitrile, dimethyl sulfoxide and dimethylformamide.

Mixtures of these can also be used.

Bases which are generally used are inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal carbonates and alkaline earth metal carbonates such as lithium carbonate, sodium carbonate, potassium carbonate and calcium carbonate and alkali metal hydrogen carbonates such as sodium hydrogen carbonate and alkali metal alcoholates and alkaline earth metal alcoholates such as sodium methanolate, sodium ethanolate, potassium ethanolate, potassium tert-butanolate and dimethoxymagnesium, and furthermore organic bases, eg. tertiary amines such as trimethylamine, triethylamine, tri-isopropylethylamine and N-methylpiperidine, pyridine, substituted pyridines such as collidine, lutidine and 4-dimethylaminopyridine and bicyclic amines.

Sodium hydride, potassium carbonate, sodium methanolate and triethylamine are particularly preferred.

The bases are generally employed in catalytic amounts, but they can also be used in equimolar amounts, in an excess or, if suitable, as the solvent.

Those starting materials required for the preparation of the compounds I have been disclosed in the literature (EP 420 091 A1; EP 38 65 561 A1; DE 36 20 860 A1; DE 35 45 318 A1; WO 93/15046 A1) or can be prepared in accordance with the literature cited.

Compounds Va where the radicals X and Y are bonded to the C atom via an oxygen, sulfur or nitrogen atom are obtained particularly advantageously by first converting a phenol ester of the formula VII in a manner known per se in an inert organic solvent with a) an alcohol, thiol and/or amine of the formula III or with b) a compound of the formula IV [or, as described above, by first converting it with trimethyl orthoformate or methanol to give the corresponding dimethyl acetal or dimethyl ketal (VIII, X=Y=OCH$_3$) and subsequently transacetalizing the product either with a compound III or a compound IV] to give the corresponding phenol ester VIII and subsequently cleaving VIII in the presence of a base to give V.

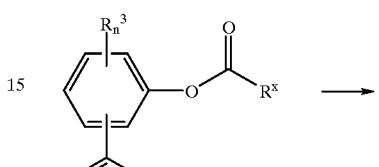

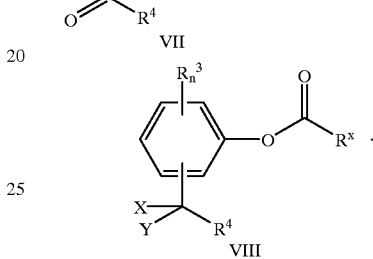

R$^x$ in formulae VII and VIII is phenyl or an alkyl group (eg. C$_1$–C$_4$-alkyl).

This ester cleavage is usually carried out at from 0° C. to 120° C., preferably 0° C. to 80° C.

Suitable solvents are, besides water, ethers such as diethyl ether, diisopropyl ether, tert-butyl methyl ether, dioxane, anisole and tetrahydrofuran, alcohols such as methanol, ethanol, n-propanol, isopropanol, n-butanol and tert-butanol, and also dimethyl sulfoxide and dimethylformamide, particularly preferably water, methanol, dimethylformamide, dimethyl sulfoxide and tetrahydrofuran. Mixtures of these can also be used.

Bases which are generally used are inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal amides such as lithium amide, sodium amide and potassium amide, alkali metal carbonates and alkaline earth metal carbonates such as sodium carbonate, potassium carbonate, calcium carbonate, alkylmagnesium halides, such as methylmagnesium chloride and alkali metal alcoholates and alkaline earth metal alcoholates such as sodium methanolate, sodium ethanolate, potassium ethanolate, potassium tert-butanolate and dimethoxymagnesium, and furthermore organic bases, eg. tertiary amines such as trimethylamine, triethylamine, tri-isopropylethylamine and N-methylpiperidine, pyridine, substituted pyridines such as collidine, lutidine and 4-dimethylaminopyridine, and bicyclic amines.

Sodium amide, sodium hydroxide, potassium hydroxide and sodium methanolate are particularly preferred.

The bases are generally employed in catalytic amounts, but they can also be used in equimolar amounts, in an excess or, if suitable, as the solvent.

The reaction mixtures are worked up in the customary manner, eg. by mixing with water, separating the phases and, if desired, purification of the crude products by chromatography. Some of the intermediates and end products are obtained in the form of colorless or pale brown, viscous oils which can be purified or freed from volatile components under reduced pressure and under moderately elevated temperature. If the intermediates and end products are obtained as solids, they can also be purified by recrystallization or digestion.

Those starting materials required according to the process described above for the preparation of the compounds I which have not already been disclosed in the literature (Polym. Commun. 337 (1984); EP 353 339 A2) can be prepared in accordance with the literature cited.

Collective terms which generally represent the following substituents are used in the definitions of the symbols given in the above formulae:

halogen: fluorine, chlorine, bromine and iodine;

alkyl: saturated, straight-chain or branched hydrocarbon radicals having 1 to 6 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 4 carbon atoms (as mentioned above), it being possible for some or all of the hydrogen atoms in these groups to be replaced by halogen atoms as mentioned above, eg. $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 6 carbon atoms (as mentioned above) which are bonded to the skeleton via an oxygen atom (—O—);

alkylthio: straight-chain or branched alkyl groups having 1 to 6 carbon atoms (as mentioned above) which are bonded to the skeleton via a sulfur atom (—S—);

alkylamino: a straight-chain or branched alkyl group having 1 to 6 carbon atoms (as mentioned above) which is bonded to the skeleton via an amino group (—NH—);

dialkylamino: an amino group which has attached to it two straight-chain or branched alkyl groups which are independent of one another and have in each case 1 to 6 carbon atoms (as mentioned above);

alkoxycarbonyl: straight-chain or branched alkyl groups having 1 to 4 carbon atoms (as mentioned above) which are bonded to the skeleton via an oxycarbonyl group (—O—CO—);

cycloalkyl: monocyclic alkyl groups having 3 to 6 carbon atom ring members, eg. cyclopropyl, cyclobutyl, cyclopentyl and cyclohexyl;

aryl: mono- or polycyclic aromatic hydrocarbons such as phenyl, naphthyl and anthracenyl; heteroaryl: mono- or polycyclic aromatic ring systems which, besides carbon atoms, can contain nitrogen, oxygen and/or sulfur atoms as ring members, eg.

5-membered heteroaryl having one to four nitrogen atoms or one to three nitrogen atoms and one sulfur or oxygen atom: 5-membered heteroaryl ring groups which, besides the carbon atoms, can have one to four nitrogen atoms or one to three nitrogen atoms and one sulfur or oxygen atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered heteroaryl having one to three nitrogen atoms or one nitrogen atom and one oxygen or sulfur atom: 5-membered heteroaryl ring groups which, besides carbon atoms, can have one to four nitrogen atoms or one to three nitrogen atoms and one sulfur or oxygen atom as ring members and in which two adjacent carbon ring members or one nitrogen and one adjacent carbon ring member can be bridged by a buta-1,3-diene-1,4-diyl group;

5-membered heteroaryl bonded by nitrogen and having one to four nitrogen atoms, or benzo-fused 5-membered heteroaryl bonded via nitrogen and having one to three nitrogen atoms: 5-membered heteroaryl ring groups which can have, besides carbon atoms, one to four nitrogen atoms, or one to three nitrogen atoms, respectively, as ring members and in which two adjacent carbon ring members or one nitrogen and one adjacent carbon ring member can be bridged by a buta-1,3-diene-1,4-diyl group, these rings being bonded to the skeleton via one of the nitrogen ring members;

6-membered heteroaryl having one to three, or one to four, nitrogen atoms: 6-membered heteroaryl ring groups which, besides carbon atoms, can have one to three, or one to four, nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Compounds I which are especially preferred are those where $R^1$ is $C(CO_2CH_3)\!=\!CHOCH_3$.

Compounds I which are also preferred are those where $R^1$ is $C(CO_2CH_3)\!=\!NOCH_3$.

Compounds I which are equally preferred are those where $R^1$ is $C(CONHCH_3)\!=\!NOCH_3$.

Compounds I which are furthermore preferred are those where $R^1$ is $N(OCH_3)\!-\!CO_2CH_3$.

Compounds I which are also particularly preferred are those where m is 0 or 1.

Compounds I which are furthermore particularly preferred are those where m is 1 and $R^2$ is cyano, fluorine, chlorine, methyl or methoxy.

Compounds I which are equally particularly preferred are those where n is 1 or 2.

Compounds I which are also particularly preferred are those where $R^3$ is halogen or $C_1$–$C_4$-alkyl.

Compounds I which are particularly preferred are those where n is 1 or 2 and the radicals $R^3$ are bonded in the 2- or 2,5-position of the phenyl ring.

Compounds I which are also especially preferred are those where the radical —CXYR⁴ is in the 4- or 5-position of the phenyl ring.

Compounds I which are furthermore particularly preferred are those where $R^4$ is hydrogen, methyl, ethyl, trifluoromethyl or cyclopropyl.

Compounds I which are equally particularly preferred are those where X is $C_1$–$C_6$-alkoxy, $C_1$–$C_6$-alkylthio, $C_1$–$C_6$-alkylamino and di-$C_1$–$C_6$-alkylamino.

Compounds I which are also particularly preferred are those where Y is $C_1$–$C_6$-alkoxy, $C_1$–$C_6$-alkylthio, $C_1$–$C_6$-alkylamino and di-$C_1$–$C_6$-alkylamino.

Compounds I which are furthermore particularly preferred are those where X and Y together with the C atom to which they are bonded are an unsubstituted or substituted oxirane ring.

Compounds I which are furthermore particularly preferred are those where X and Y are an unsubstituted or substituted $C_2$–$C_4$-alkylene chain which is bonded to the carbon atom via oxygen, sulfur and/or nitrogen atoms.

Equally preferred are compounds I where X and Y together with the C atom to which they are bonded are one of the following heterocycles XY.1 to XY.9:

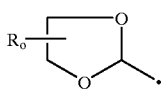 XY.1

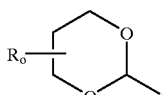 XY.2

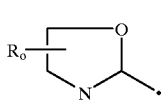 XY.3

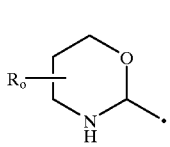 XY.4

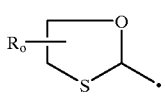 XY.5

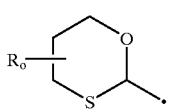 XY.6

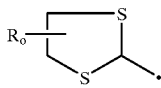 XY.7

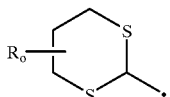 XY.8

 XY.9 where the bond marked ● bond to the phenyl ring and where
  o is 0, 1, 2 or 3, it being possible for the substituents R to be different from each other when o is 2 or 3; and
  R is $C_1$–$C_4$-alkyl, $C_3$–$C_6$-cycloalkyl, $C_1$–$C_4$-alkoxycarbonyl, aryl, cyano and heteroaryl or where one or more $CH_2$ groups of the alkylene chain can be replaced by C=O.

Compounds which are especially preferred are those of the formula I.A

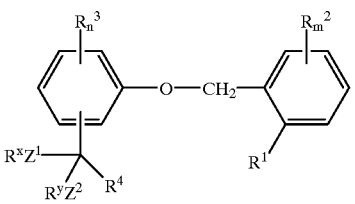

I.A where the substituents have the following meanings:
  $R^1$ is $C(CO_2CH_3)$=$CHOCH_3$, $C(CO_2CH_3)$=$NOCH_3$, $N(OCH_3)CO_2CH_3$ and $C(CONHCH_3)$=$NOCH_3$;
  $R^2$ is cyano, halogen, $C_1$–$C_4$-alkyl and $C_1$–$C_4$-alkoxy;
  m is 0, 1 or 2, it being possible for the substituents $R^2$ to be different from each other when m is 2;
  $R^3$ is cyano, halogen, $C_1$–$C_4$-alkyl, $C_1$–$C_4$-haloalkyl and $C_1$–$C_4$-alkoxy;
  n is 0, 1, 2 or 3, it being possible for the substituents $R^3$ to be different from each other when n is 2 or 3;
  $R^4$ is hydrogen, $C_1$–$C_4$-alkyl, $C_1$–$C_4$-haloalkyl, $C_3$–$C_6$-cycloalkyl and phenyl;
  $Z^1$ and $Z^2$ are oxygen, sulfur, amino (NH) or $C_1$–$C_6$-alkylamino; and
  $R^x$ and $R^y$ are $C_1$–$C_6$-alkyl.

Compounds which are furthermore especially preferred are those of the formula I.B

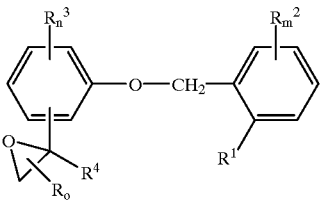

I.B where the substituents have the following meanings:
  $R^1$ is $C(CO_2CH_3)$=$CHOCH_3$, $C(CO_2CH_3)$=$NOCH_3$, $N(OCH_3)CO_2CH_3$ and $C(CONHCH_3)$=$NOCH_3$;
  $R^2$ is cyano, halogen, $C_1$–$C_4$-alkyl and $C_1$–$C_4$-alkoxy;
  m is 0, 1 or 2, it being possible for the substituents $R^2$ to be different from each other when m is 2;
  $R^3$ is cyano, halogen, $C_1$–$C_4$-alkyl, $C_1$–$C_4$-haloalkyl and $C_1$–$C_4$-alkoxy;
  n is 0, 1, 2 or 3, it being possible for the substituents $R^3$ to be different from each other when n is 2 or 3;

$R^4$ is hydrogen, $C_1$–$C_4$-alkyl, $C_1$–$C_4$-haloalkyl, $C_3$–$C_6$-cycloalkyl and phenyl;

o is 0.

Compounds which are also especially preferred are those of the formula I.C

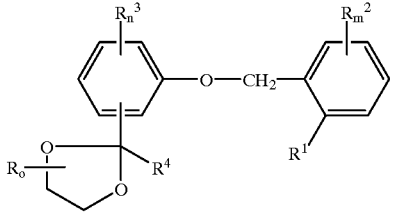

I.C where the substituents have the following meanings:
$R^1$ is $C(CO_2CH_3)$=$CHOCH_3$, $C(CO_2CH_3)$=$NOCH_3$, $N(OCH_3)CO_2CH_3$ and $C(CONHCH_3)$=$NOCH_3$;
$R^2$ is cyano, halogen, $C_1$–$C_4$-alkyl and $C_1$–$C_4$-alkoxy;
m is 0, 1 or 2, it being possible for the substituents $R^2$ to be different from each other when m is 2;
$R^3$ is cyano, halogen, $C_1$–$C_4$-alkyl, $C_1$–$C_4$-haloalkyl and $C_1$–$C_4$-alkoxy;
n is 0, 1, 2 or 3, it being possible for the substituents $R^3$ to be different from each other when n is 2 or 3;
$R^4$ is hydrogen, $C_1$–$C_4$-alkyl, $C_1$–$C_4$-haloalkyl, $C_3$–$C_6$-cycloalkyl and phenyl;
o is 0, 1, 2 or 3, it being possible for the substituents R to be different from each other when o is 2 or 3; and
R is $C_1$–$C_4$-alkyl, $C_3$–$C_6$-cycloalkyl, $C_1$–$C_4$-alkoxycarbonyl, cyano, aryl and heteroaryl or where a $CH_2$ group of the alkylene chain can be replaced by C=O.

Compounds which are furthermore especially preferred are those of the formula I.D

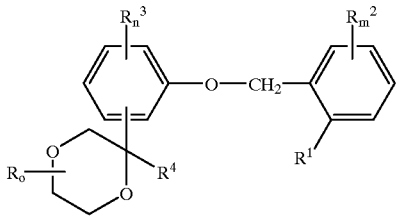

I.D where the substituents have the following meanings:
$R^1$ is $C(CO_2CH_3)$=$CHOCH_3$, $C(CO_2CH_3)$=$NOCH_3$, $N(OCH_3)CO_2CH_3$ and $C(CONHCH_3)$=$NOCH_3$;
$R^2$ is cyano, halogen, $C_1$–$C_4$-alkyl and $C_1$–$C_4$-alkoxy;
m is 0, 1 or 2, it being possible for the substituents $R^2$ to be different from each other when m is 2;
$R^3$ is cyano, halogen, $C_1$–$C_4$-alkyl, $C_1$–$C_4$-haloalkyl and $C_1$–$C_4$-alkoxy;
n is 0, 1, 2 or 3, it being possible for the substituents $R^3$ to be different from each other when n is 2 or 3;
$R^4$ is hydrogen, $C_1$–$C_4$-alkyl, $C_1$–$C_4$-haloalkyl, $C_3$–$C_6$-cycloalkyl and phenyl;
o is 0, 1, 2 or 3, it being possible for the substituents R to be different from each other when o is 2 or 3; and
R is $C_1$–$C_4$-alkyl, $C_3$–$C_6$-cycloalkyl, $C_1$–$C_4$-alkoxycarbonyl, cyano, aryl and heteroaryl or where a $CH_2$ group of the alkylene chain can be replaced by C=O.

Compounds which are also especially preferred are those of the formula I.E

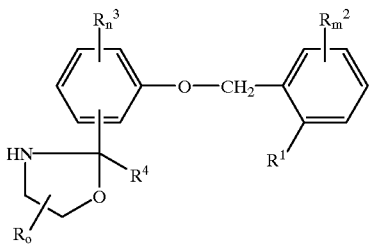

I.E where the substituents have the following meanings:
$R^1$ is $C(CO_2CH_3)$=$CHOCH_3$, $C(CO_2CH_3)$=$NOCH_3$, $N(OCH_3)CO_2CH_3$ and $C(CONHCH_3)$=$NOCH_3$;
$R^2$ is cyano, halogen, $C_1$–$C_4$-alkyl and $C_1$–$C_4$-alkoxy;
m is 0, 1 or 2, it being possible for the substituents $R^2$ to be different from each other when m is 2;
$R^3$ is cyano, halogen, $C_1$–$C_4$-alkyl, $C_1$–$C_4$-haloalkyl and $C_1$–$C_4$-alkoxy;
n is 0, 1, 2 or 3, it being possible for the substituents $R^3$ to be different from each other when n is 2 or 3;
$R^4$ is hydrogen, $C_1$–$C_4$-alkyl, $C_1$–$C_4$-haloalkyl, $C_3$–$C_6$-cycloalkyl and phenyl;
o is 0, 1, 2 or 3, it being possible for the substituents R to be different from each other when o is 2 or 3; and
R is $C_1$–$C_4$-alkyl, $C_3$–$C_6$-cycloalkyl, $C_1$–$C_4$-alkoxycarbonyl, cyano, aryl and heteroaryl or where a $CH_2$ group of the alkylene chain can be replaced by C=O.

Compounds which are furthermore especially preferred are those of the formula I.F

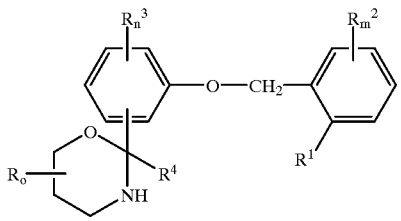

I.F where the substituents have the following meanings:
$R^1$ is $C(CO_2CH_3)$=$CHOCH_3$, $C(CO_2CH_3)$=$NOCH_3$, $N(OCH_3)CO_2CH_3$ and $C(CONHCH_3)$=$NOCH_3$;
$R^2$ is cyano, halogen, $C_1$–$C_4$-alkyl and $C_1$–$C_4$-alkoxy;
m is 0, 1 or 2, it being possible for the substituents $R^2$ to be different from each other when m is 2;
$R^3$ is cyano, halogen, $C_1$–$C_4$-alkyl, $C_1$–$C_4$-haloalkyl and $C_1$–$C_4$-alkoxy;
n is 0, 1, 2 or 3, it being possible for the substituents $R^3$ to be different from each other when n is 2 or 3;
$R^4$ is hydrogen, $C_1$–$C_4$-alkyl, $C_1$–$C_4$-haloalkyl, $C_3$–$C_6$-cycloalkyl and phenyl;
o is 0, 1, 2 or 3, it being possible for the substituents R to be different from each other when o is 2 or 3; and
R is $C_1$–$C_4$-alkyl, $C_3$–$C_6$-cycloalkyl, $C_1$–$C_4$-alkoxycarbonyl, cyano, aryl and heteroaryl or where a $CH_2$ group of the alkylene chain can be replaced by C=O.

Compounds which are also especially preferred are those of the formula I.G

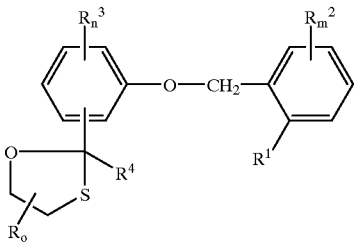

I.G where the substituents have the following meanings:
$R^1$ is $C(CO_2CH_3)=CHOCH_3$, $C(CO_2CH_3)=NOCH_3$, $N(OCH_3)CO_2CH_3$ and $C(CONHCH_3)=NOCH_3$;
$R^2$ is cyano, halogen, $C_1$–$C_4$-alkyl and $C_1$–$C_4$-alkoxy;
m is 0, 1 or 2, it being possible for the substituents $R^2$ to be different from each other when m is 2;
$R^3$ is cyano, halogen, $C_1$–$C_4$-alkyl, $C_1$–$C_4$-haloalkyl and $C_1$–$C_4$-alkoxy;
n is 0, 1, 2 or 3, it being possible for the substituents $R^3$ to be different from each other when n is 2 or 3;
$R^4$ is hydrogen, $C_1$–$C_4$-alkyl, $C_1$–$C_4$-haloalkyl, $C_3$–$C_6$-cycloalkyl and phenyl;
o is 0, 1, 2 or 3, it being possible for the substituents R to be different from each other when o is 2 or 3; and
R is $C_1$–$C_4$-alkyl, $C_3$–$C_6$-cycloalkyl, $C_1$–$C_4$-alkoxycarbonyl, cyano, aryl and heteroaryl or where a $CH_2$ group of the alkylene chain can be replaced by C=O.

Compounds which are furthermore especially preferred are those of the formula I.H

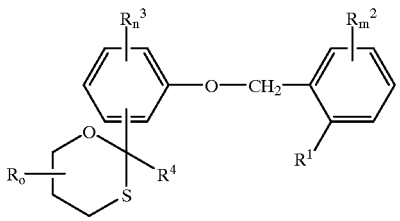

I.H where the substituents have the following meanings:
$R^1$ is $C(CO_2CH_3)=CHOCH_3$, $C(CO_2CH_3)=NOCH_3$, $N(OCH_3)CO_2CH_3$ and $C(CONHCH_3)=NOCH_3$;
$R^2$ is cyano, halogen, $C_1$–$C_4$-alkyl and $C_1$–$C_4$-alkoxy;
m is 0, 1 or 2, it being possible for the substituents $R^2$ to be different from each other when m is 2;
$R^3$ is cyano, halogen, $C_1$–$C_4$-alkyl, $C_1$–$C_4$-haloalkyl and $C_1$–$C_4$-alkoxy;
n is 0, 1, 2 or 3, it being possible for the substituents $R^3$ to be different from each other when n is 2 or 3;
$R^4$ is hydrogen, $C_1$–$C_4$-alkyl, $C_1$–$C_4$-haloalkyl, $C_3$–$C_6$-cycloalkyl and phenyl;
o is 0, 1, 2 or 3, it being possible for the substituents R to be different from each other when o is 2 or 3; and
R is $C_1$–$C_4$-alkyl, $C_3$–$C_6$-cycloalkyl, $C_1$–$C_4$-alkoxycarbonyl, cyano, aryl and heteroaryl or where a $CH_2$ group of the alkylene chain can be replaced by C=O.

Compounds which are also especially preferred are those of the formula I.K

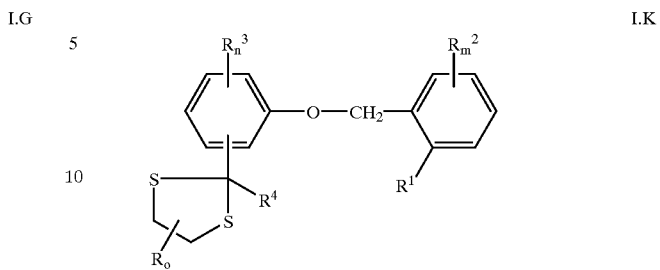

I.K where the substituents have the following meanings:
$R^1$ is $C(CO_2CH_3)=CHOCH_3$, $C(CO_2CH_3)=NOCH_3$, $N(OCH_3)CO_2CH_3$ and $C(CONHCH_3)=NOCH_3$;
$R^2$ is cyano, halogen, $C_1$–$C_4$-alkyl and $C_1$–$C_4$-alkoxy;
m is 0, 1 or 2, it being possible for the substituents $R^2$ to be different from each other when m is 2;
$R^3$ is cyano, halogen, $C_1$–$C_4$-alkyl, $C_1$–$C_4$-haloalkyl and $C_1$–$C_4$-alkoxy;
n is 0, 1, 2 or 3, it being possible for the substituents $R^3$ to be different from each other when n is 2 or 3;
$R^4$ is hydrogen, $C_1$–$C_4$-alkyl, $C_1$–$C_4$-haloalkyl, $C_3$–$C_6$-cycloalkyl and phenyl;
o is 0, 1, 2 or 3, it being possible for the substituents R to be different from each other when o is 2 or 3; and
R is $C_1$–$C_4$-alkyl, $C_3$–$C_6$-cycloalkyl, $C_1$–$C_4$-alkoxycarbonyl, aryl and heteroaryl or where a $CH_2$ group of the alkylene chain can be replaced by C=O.

Compounds which are also especially preferred are those of the formula I.L

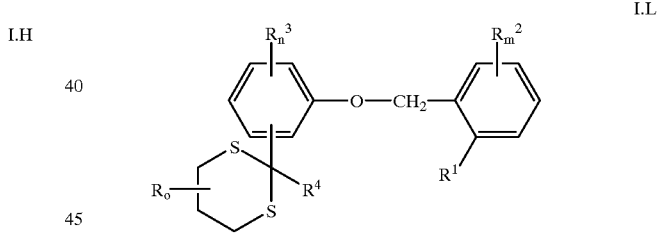

I.L where the substituents have the following meanings:
$R^1$ is $C(CO_2CH_3)=CHOCH_3$, $C(CO_2CH_3)=NOCH_3$, $N(OCH_3)CO_2CH_3$ and $C(CONHCH_3)=NOCH_3$;
$R^2$ is cyano, halogen, $C_1$–$C_4$-alkyl and $C_1$–$C_4$-alkoxy;
m is 0, 1 or 2, it being possible for the substituents $R^2$ to be different from each other when m is 2;
$R^3$ is cyano, halogen, $C_1$–$C_4$-alkyl, $C_1$–$C_4$-haloalkyl and $C_1$–$C_4$-alkoxy;
n is 0, 1, 2 or 3, it being possible for the substituents $R^3$ to be different from each other when n is 2 or 3;
$R^4$ is hydrogen, $C_1$–$C_4$-alkyl, $C_1$–$C_4$-haloalkyl, $C_3$–$C_6$-cycloalkyl and phenyl;
o is 0, 1, 2 or 3, it being possible for the substituents R to be different from each other when o is 2 or 3; and
R is $C_1$–$C_4$-alkyl, $C_3$–$C_6$-cycloalkyl, $C_1$–$C_4$-alkoxycarbonyl, aryl and heteroaryl or where a $CH_2$ group of the alkylene chain can be replaced by C=O.

Compounds I which are especially preferred with a view to their use are those compiled in the tables which follow.

Moreover, the groups mentioned for a substituent in the tables, on their own (independently of the combination in which they are mentioned), are considered a particularly preferred embodiment of the substituent in question.

Table 1

Compounds of the general formula I.1 where m is 0, $R^3_n$ is 2-methyl and the combination of the substituents X, Y and $R^4$ for a compound is in each case one line of Table A, the group —CXYR$^4$ being bonded in the 4-position of the phenyl ring.

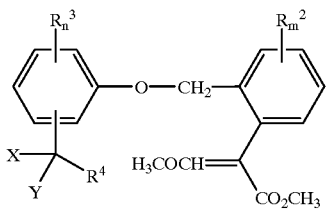

I.1

Table 2

Compounds of the general formula I.2 where m is 0, $R^3_n$ is 2-methyl and the combination of the substituents X, Y and $R^4$ for a compound is in each case one line of Table A, the group —CXYR$^4$ being bonded in the 4-position of the phenyl ring.

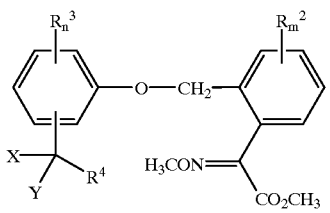

I.2

Table 3

Compounds of the general formula I.3 where m is 0, $R^3_n$ is 2-methyl and the combination of the substituents X, Y and $R^4$ for a compound is in each case one line of Table A, the group —CXYR$^4$ being bonded in the 4-position of the phenyl ring.

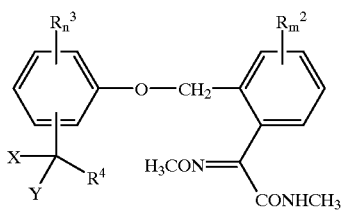

I.3

Table 4

Compounds of the general formula I.4 where m is 0, $R^3_n$ is 2-methyl and the combination of the substituents X, Y and $R^4$ for a compound is in each case one line of Table A, the group —CXYR$^4$ being bonded in the 4-position of the phenyl ring.

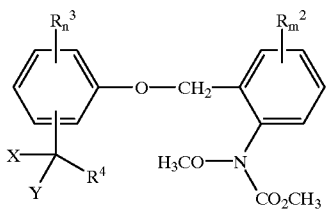

I.4

Table 5

Compounds of the general formula I.1 where m is 0, $R^3_n$ is 2-methyl and the combination of the substituents X, Y and $R^4$ for a compound is in each case one line of Table A, the group —CXYR$^4$ being bonded in the 5-position of the phenyl ring.

Table 6

Compounds of the general formula I.2 where m is 0, $R^3_n$ is 2-methyl and the combination of the substituents X, Y and $R^4$ for a compound is in each case one line of Table A, the group —CXYR$^4$ being bonded in the 5-position of the phenyl ring.

Table 7

Compounds of the general formula I.3 where m is 0, $R^3_n$ is 2-methyl and the combination of the substituents X, Y and $R^4$ for a compound is in each case one line of Table A, the group —CXYR$^4$ being bonded in the 5-position of the phenyl ring.

Table 8

Compounds of the general formula I.4 where m is 0, $R^3_n$ is 2-methyl and the combination of the substituents X, Y and $R^4$ for a compound is in each case one line of Table A, the group —CXYR$^4$ being bonded in the 5-position of the phenyl ring.

Table 9

Compounds of the general formula I.1 where m is 0, $R^3_n$ is 2-fluoro and the combination of the substituents X, Y and $R^4$ for a compound is in each case one line of Table A, the group —CXYR$^4$ being bonded in the 4-position of the phenyl ring.

Table 10

Compounds of the general formula I.2 where m is 0, $R^3_n$ is 2-fluoro and the combination of the substituents X, Y and $R^4$ for a compound is in each case one line of Table A, the group —CXYR$^4$ being bonded in the 4-position of the phenyl ring.

Table 11

Compounds of the general formula I.3 where m is 0, $R^3_n$ is 2-fluoro and the combination of the substituents X, Y and $R^4$ for a compound is in each case one line of Table A, the group —CXYR$^4$ being bonded in the 4-position of the phenyl ring.

Table 12

Compounds of the general formula I.4 where m is 0, $R^3_n$ is 2-fluoro and the combination of the substituents X, Y and $R^4$ for a compound is in each case one line of Table A, the group —CXYR$^4$ being bonded in the 4-position of the phenyl ring.

Table 13

Compounds of the general formula I.1 where m is 0, $R^3_n$ is 2-fluoro and the combination of the substituents X, Y and $R^4$ for a compound is in each case one line of Table A, the group —CXYR$^4$ being bonded in the 5-position of the phenyl ring.

Table 14

Compounds of the general formula I.2, where m is 0, $R^3_n$ is 2-fluoro and the combination of the substituents X, Y and Table 15

Compounds of the general formula I.3, where m is 0, $R^3{}_n$ is 2-fluoro and the combination of the substituents X, Y and $R^4$ for a compound is in each case one line of Table A, the group —$CXYR^4$ being bonded in the 5-position of the phenyl ring.

Table 16

Compounds of the general formula I.4, where m is 0, $R^3{}_n$ is 2-fluoro and the combination of the substituents X, Y and $R^4$ for a compound is in each case one line of Table A, the group —$CXYR^4$ being bonded in the 5-position of the phenyl ring.

Table 17

Compounds of the general formula I.1, where m is 0, $R^3{}_n$ is 2,5-dimethyl and the combination of the substituents X, Y and $R^4$ for a compound is in each case one line of Table A, the group —$CXYR^4$ being bonded in the 4-position of the phenyl ring.

Table 18

Compounds of the general formula I.2, where m is 0, $R^3{}_n$ is 2,5-dimethyl and the combination of the substituents X, Y and $R^4$ for a compound is in each case one line of Table A, the group —$CXYR^4$ being bonded in the 4-position of the phenyl ring.

Table 19

Compounds of the general formula I.3, where m is 0, $R^3{}_n$ is 2,5-dimethyl and the combination of the substituents X, Y and $R^4$ for a compound is in each case one line of Table A, the group —$CXYR^4$ being bonded in the 4-position of the phenyl ring.

Table 20

Compounds of the general formula I.4, where m is 0, $R^3{}_n$ is 2,5-dimethyl and the combination of the substituents X, Y and $R^4$ for a compound is in each case one line of Table A, the group —$CXYR^4$ being bonded in the 4-position of the phenyl ring.

Table 21

Compounds of the general formula I.1, where m is 0, $R^3{}_n$ is 2-methyl, 5-chloro and the combination of the substituents X, Y and $R^4$ for a compound is in each case one line of Table A, the group —$CXYR^4$ being bonded in the 4-position of the phenyl ring.

Table 22

Compounds of the general formula I.2, where m is 0, $R^3{}_n$ is 2-methyl, 5-chloro and the combination of the substituents X, Y and $R^4$ for a compound is in each case one line of Table A, the group —$CXYR^4$ being bonded in the 4-position of the phenyl ring.

Table 23

Compounds of the general formula I.3, where m is 0, $R^3{}_n$ is 2-methyl, 5-chloro and the combination of the substituents X, Y and $R^4$ for a compound is in each case one line of Table A, the group —$CXYR^4$ being bonded in the 4-position of the phenyl ring.

Table 24

Compounds of the general formula I.4, where m is 0, $R^3{}_n$ is 2-methyl, 5-chloro and the combination of the substituents X, Y and $R^4$ for a compound is in each case one line of Table A, the group —$CXYR^4$ being bonded in the 4-position of the phenyl ring.

Table 25

Compounds of the general formula I.1, where m is 0, $R^3{}_n$ is 2,5-dichloro and the combination of the substituents X, Y and $R^4$ for a compound is in each case one line of Table A, the group —$CXYR^4$ being bonded in the 4-position of the phenyl ring.

Table 26

Compounds of the general formula I.2, where m is 0, $R^3{}_n$ is 2,5-dichloro and the combination of the substituents X, Y and $R^4$ for a compound is in each case one line of Table A, the group —$CXYR^4$ being bonded in the 4-position of the phenyl ring.

Table 27

Compounds of the general formula I.3, where m is 0, $R^3{}_n$ is 2,5-dichloro and the combination of the substituents X, Y and $R^4$ for a compound is in each case one line of Table A, the group —$CXYR^4$ being bonded in the 4-position of the phenyl ring.

Table 28

Compounds of the general formula I.4, where m is 0, $R^3{}_n$ is 2,5-dichloro and the combination of the substituents X, Y and $R^4$ for a compound is in each case one line of Table A, the group —$CXYR^4$ being bonded in the 4-position of the phenyl ring.

Table 29

Compounds of the general formula I.1, where m and n are 0, and the combination of the substituents X, Y and $R^4$ for a compound is in each case one line of Table A, the group —$CXYR^4$ being bonded in the 4-position of the phenyl ring.

Table 30

Compounds of the general formula I.2, where m and n are 0 and the combination of the substituents X, Y and $R^4$ for a compound is in each case one line of Table A, the group —$CXYR^4$ being bonded in the 4-position of the phenyl ring.

Table 31

Compounds of the general formula I.3, where m and n are 0 and the combination of the substituents X, Y and $R^4$ for a compound is in each case one line of Table A, the group —$CXYR^4$ being bonded in the 4-position of the phenyl ring.

Table 32

Compounds of the general formula I.4, where m and n are 0 and the combination of the substituents X, Y and $R^4$ for a compound is in each case one line of Table A, the group —$CXYR^4$ being bonded in the 4-position of the phenyl ring.

Table 33

Compounds of the general formula I.1, where m and n are 0 and the combination of the substituents X, Y and $R^4$ for a compound is in each case one line of Table A, the group —$CXYR^4$ being bonded in the 5-position of the phenyl ring.

Table 34

Compounds of the general formula I.2, where m and n are 0 and the combination of the substituents X, Y and $R^4$ for a compound is in each case one line of Table A, the group —$CXYR^4$ being bonded in the 5-position of the phenyl ring.

Table 35

Compounds of the general formula I.3, where m and n are 0 and the combination of the substituents X, Y and $R^4$ for a compound is in each case one line of Table A, the group —$CXYR^4$ being bonded in the 5-position of the phenyl ring.

Table 36

Compounds of the general formula I.4, where m and n are 0 and the combination of the substituents X, Y and $R^4$ for a compound is in each case one line of Table A, the group —$CXYR^4$ being bonded in the 5-position of the phenyl ring.

TABLE A

|    | X         | Y         | $R^4$      |
|----|-----------|-----------|------------|
| 01 | $OCH_3$   | $OCH_3$   | H          |
| 02 | $OCH_3$   | $OCH_3$   | $CH_3$     |
| 03 | $OCH_3$   | $OCH_3$   | $CH_2CH_3$ |
| 04 | $OCH_2CH_3$ | $OCH_2CH_3$ | H        |

TABLE A-continued

| | X | Y | R⁴ |
|---|---|---|---|
| 05 | OCH₂CH₃ | OCH₂CH₃ | CH₃ |
| 06 | OCH₂CH₃ | OCH₂CH₃ | CH₂CH₃ |
| 07 | | CH₂O | H |
| 08 | | CH₂O | CH₃ |
| 09 | | CH₂O | CH₂CH₃ |
| 10 | | OCH₂CH₂O | H |
| 11 | | OCH₂CH₂O | CH₃ |
| 12 | | OCH₂CH₂O | CH₂CH₃ |
| 13 | | OCH₂CH₂CH₂O | H |
| 14 | | OCH₂CH₂CH₂O | CH₃ |
| 15 | | OCH₂CH₂CH₂O | CH₂CH₃ |
| 16 | | CH(CH₃)O | H |
| 17 | | CH(CH₃)O | CH₃ |
| 18 | | CH(CH₃)O | CH₂CH₃ |
| 19 | | OC(=O)CH₂O | H |
| 20 | | OC(=O)CH₂O | CH₃ |
| 21 | | OC(=O)CH₂O | CH₂CH₃ |
| 22 | | OC(=O)CH₂CH₂O | H |
| 23 | | OC(=O)CH₂CH₂O | CH₃ |
| 24 | | OC(=O)CH₂CH₂O | CH₂CH₃ |
| 25 | | OCH₂CH₂S | H |
| 26 | | OCH₂CH₂S | CH₃ |
| 27 | | OCH₂CH₂S | CH₂CH₃ |
| 28 | | SCH₂CH₂S | H |
| 29 | | SCH₂CH₂S | CH₃ |
| 30 | | SCH₂CH₂S | CH₂CH₃ |
| 31 | | SCH₂CH₂CH₂S | H |
| 32 | | SCH₂CH₂CH₂S | CH₃ |
| 33 | | SCH₂CH₂CH₂S | CH₂CH₃ |
| 34 | | OCH₂CH₂CH₂S | H |
| 35 | | OCH₂CH₂CH₂S | CH₃ |
| 36 | | OCH₂CH₂CH₂S | CH₂CH₃ |
| 37 | | OCH(CH₃)CH₂O | H |
| 38 | | OCH(CH₃)CH₂O | CH₃ |
| 39 | | OCH(CH₃)CH₂O | CH₂CH₃ |
| 40 | | OCH(CH₃)CH(CH₃)O | H |
| 41 | | OCH(CH₃)CH(CH₃)O | CH₃ |
| 42 | | OCH(CH₃)CH(CH₃)O | CH₂CH₃ |
| 43 | | OCH(CH₂CH₃)CH(CH₂CH₃)O | H |
| 44 | | OCH(CH₂CH₃)CH(CH₂CH₃)O | CH₃ |
| 45 | | OCH(CH₂CH₃)CH(CH₂CH₃)O | CH₂CH₃ |

The compounds I are suitable for use as fungicides.

The compounds I are distinguished by an outstanding activity against a wide spectrum of phytopathogenic fungi, in particular from the classes of the Ascomycetes and Basidiomycetes. Some of them act systemically and can be employed as foliar- and soil-acting fungicides.

They are particularly important for controlling a large number of fungi in a variety of crop plants such as wheat, rye, barley, oats, rice, maize, grass, cotton, soya, coffee, sugar cane, grape vine, fruit species, ornamentals and vegetable species such as cucumbers, beans and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grape vines, Puccinia species in cereals, Rhizoctonia species in cotton and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries and grape vines, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in a variety of plants, *Plasmopara viticola* in grape vines, Alternaria species in vegetables and fruit.

The compounds I are used by treating the fungi, or the plants, seeds, materials or the soil to be treated against fungal infection, with a fungicidally active amount of the active ingredients. Application is effected before or after infection of the materials, plants or seeds by the fungi.

They can be converted into the customary formulations, such as solutions, emulsions, suspensions, dusts, powders, pastes and granules. The use form depends on the intended purpose in question; in any case, it should guarantee fine and uniform distribution of the compounds according to the invention. The formulations are prepared in a known manner, eg. by extending the active ingredient with solvents and/or carriers, if desired using emulsifiers and dispersants, it also being possible to use other organic solvents as auxiliary solvents if water is used as the diluent. Suitable auxiliaries are essentially: solvents, such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as non-ionic and anionic emulsifiers (eg. polyoxyethylene fatty alcohol ethers, alkylsulfonates and arylsulfonates) and dispersants such as lignosulfite waste liquors and methylcellulose.

The fungicidal compositions generally comprise from 0.1 to 95, preferably from 0.5 to 90, % by weight of active ingredient.

Depending on the nature of the desired effect, the rates of application are from 0.01 to 2.0 kg of active ingredient per ha.

In the treatment of seed, amounts of from 0.001 to 0.1 g, preferably 0.01 to 0.05 g, of active ingredient are generally required per kilogram of seed.

In the use form as fungicides, the compositions according to the invention can also be present together with other active ingredients, eg. with herbicides, insecticides, growth regulators, fungicides or else with fertilizers.

In many cases, a mixture with other fungicides widens the fungicidal spectrum of action.

The following list of fungicides together with which the compounds according to the invention can be applied is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl) disulfide;

nitro derivatives, such as dinitro(1-methylheptyl)phenyl crotonate, 2-sec-butyl-4,6-dinitrophenyl-3,3-dimethyl acrylate, 2-sec-butyl-4,6-dinitrophenyl isopropylcarbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2))-benzimidazole, 2-(thiazolyl-(4))-benzimidazole, N-(1, 1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,4-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-2,2,2-trichloro-1-(4-morpholinyl)ethylformamide, piperazine-1,4-diylbis(1-(2,2,2-trichloroethyl) formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides such as dodecylguanidine acetate, 3-[3-(3,5-dimethyl-2-oxycyclohexyl)-2-hydroxyethyl]glutarimide, hexachlorobenzene, DL-methyl N-(2,6-dimethylphenyl)-N-furoyl(2)-alaninate, DL-methyl N-(2,6-dimethylphenyl)-N-(2'-methoxyacetyl)-alaninate, N-(2,6-dimethylphenyl)-N-chloroacetyl-D,L-2-aminobutyrolactone, DL-methyl N-(2,6-dimethylphenyl)-N-(phenylacetyl)-alaninate, 5-methyl-5-vinyl-3-(3,5-dichlorophenyl)-2,4-dioxo-1,3-oxazolidine, 3-[3,5-dichlorophenyl(5-methyl-5-methoxymethyl]-1,3-oxazolidine 2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis (4-fluorophenyl) methylsilyl)methyl)-1H-1,2,4-triazole.

The compounds of the formula I are furthermore suitable for efficiently controlling pests from the classes of insects, arachnids and nematodes. They can be employed as pesticides in crop protection and in the hygiene, stored-product and veterinary sectors.

The harmful insects include: from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus soistitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta* texana, Hoplocampa minuta, Hoplocampa testudinea, Monomorium pharaonis, Solenopsis geminata, Solenopsis invicta.

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root knot nematodes, eg. *Meloidogyne hapla, Meloidogyne incognita, Meloidogyne javanica,* cystdenematodes, eg. *Globodera rostochiensis, Heterodera avenae, Heterodera glycines, Heterodera schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be used as such, in the form of their formulations or in the form of the use forms prepared therefrom, eg. in the form of ready-to-spray solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, they should guarantee the finest possible distribution of the active ingredients according to the invention.

The concentrations of active ingredient in the ready-to-use preparations can be varied within wide ranges.

They are in general from 0.0001 to 10%, preferably from 0.01 to 1%.

The active ingredients can also be used very successfully in the ultra-low-volume method (ULV), it being possible to apply formulations comprising more than 95% by weight of active ingredient, or even the active ingredient without additives.

The application rate of active ingredient for controlling pests is 0.1 to 2.0, preferably 0.2 to 1.0, kg/ha under field conditions.

The substances which are suitable for preparing ready-to-spray solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agent, adhesive, dispersant or emulsifier. Alternatively, it is also possible to prepare concentrates composed of active substance, wetting agent, adhesive, dispersant or emulsifier and, if desired, solvent or oil, and these concentrates are suitable for dilution with water.

Suitable surfactants are alkali metal salts, alkaline earth metal salts and ammonium salts of lignosulfonic acid, naphthalenesulfonic acid, phenolsulfonic acid, dibutylnaphthalenesulfonic acid or alkylarylsulfonates, alkyl sulfates, alkylsulfonates, fatty alcohol sulfates and fatty acids and their alkali metal and alkaline earth metal salts, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Powders, materials for spreading and dusts can be prepared by mixing or grinding the active ingredients together with a solid carrier.

The formulations in general comprise from 0.01 to 95% by weight, preferably from 0.1 to 90% by weight, of the active ingredient. The active ingredients are employed in a purity of from 90% to 100%, preferably 95% to 100% (in accordance with NMR spectrum).

Examples of formulations are:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of a pulverulent silica gel and 8 parts by weight of paraffin oil with which the surface of this silica gel has been sprayed. This gives a preparation of the active ingredient with good adherence properties (comprises 23% by weight of active ingredient).

III. 10 parts by weight of a compound according to the invention are dissolved in a mixture which is composed of 90 parts by weight of xylene, 6 parts by weight of the adduct of 8 to 10 mol of ethylene oxide to 1 mol of oleic acid N-monoethanolamide, 2 parts by weight of calcium dodecylbenzenesulfonate and 2 parts by weight of the adduct of 40 mol of ethylene oxide to 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide to 1 mol of isooctylphenol and 5 parts by weight of the adduct of 40 mol of ethylene oxide to 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, the mixture is ground in a hammer mill (comprises 80% by weight of active ingredient).

VI. 90 parts by weight of a compound according to the invention are mixed with 10 parts by weight of N-methyl-α-pyrrolidone, and this gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients to solid carriers. Examples of solid carriers are mineral earths such as silica gel, silicas, silica gels, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, eg. ammonium sulfate, ammonium phosphate, ammonium nitrate, ureas and products of vegetable origin, such as cereal meal, tree bark meal, wood meal and nutshell meal, cellulose powders and other solid carriers.

Various types of oils, or herbicides, fungicides, other pesticides and bactericides can be admixed with the active ingredients, if desired only immediately before use (tank mix). These agents can be admixed with the agents according to the invention in a weight ratio of 1:10 to 10:1.

SYNTHESIS EXAMPLES

The protocols given in the synthesis examples below were used for obtaining other compounds I by changing the starting materials accordingly. The resulting compounds together with physical data are given in the Tables which follow.

Example 1

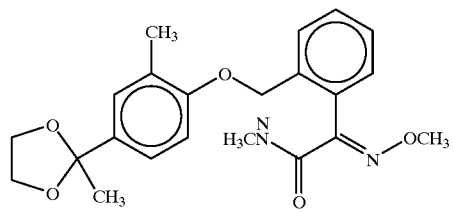

3.5 g of N-methyl-2-[(2'-methyl-4'-acetyl) phenoxymethyl]-phenylglyoxylamide O-methyl oxime (for preparation, cf. DE 43 12 637 A1) together with 0.7 g of ethylene glycol, 1.1 g of trimethyl orthoformate and 1 drop of methanesulfonic acid are stirred for 24 hours at RT (~25° C.). For working up, the mixture is treated with 0.3 g of 30% strength $NaOCH_3$ solution in methanol, and extracted with water, and the organic phase is concentrated. The residue is crystallized by stirring with diisopropyl ether. This gives 2.5 g of the title compound of melting point 94–97° C.

Example 2

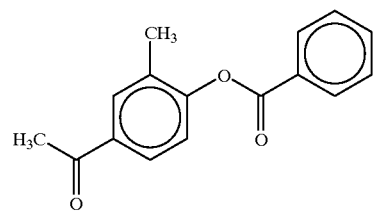

174 g of pyridine followed by 309.3 g of benzoyl chloride are added dropwise to 300.4 g of 4-acetyl-2-methylphenol. After 1 hour at 40° C., the mixture is taken up in dilute hydrochloric acid, extracted 1× using dilute hydrochloric acid, 2× using $NaHCO_3$ and 2× using water, dried and concentrated. 514.8 g remain, and this is crystallized by stirring with diisopropyl ether. IR $(cm^{-1})$=1734, 1684, 1268, 1129, 699.

Example 3

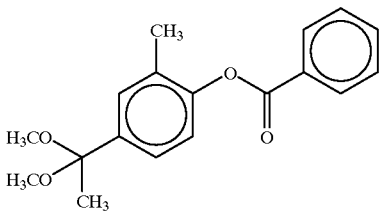

170.4 g of the compound of Example 2 are dissolved in 300 ml of methylene chloride, and the solution is treated with 78.2 g of trimethyl orthoformate and 0.2 g of methanesulfonic acid. After 120 hours at room temperature (RT), a further 3 g of methanesulfonic acid are added and the mixture is stirred for a further 10 hours at RT. The mixture is subsequently treated with 30% strength NaOCH₃ solution (pH 9), concentrated, taken up in tert-butyl methyl ether, washed 1× using saturated NH₄Cl solution, 3× using saturated NaHCO₃ solution and 2× using water, dried and concentrated. This gives 226 g of product which is employed in Example 4 without further purification.

Example 4

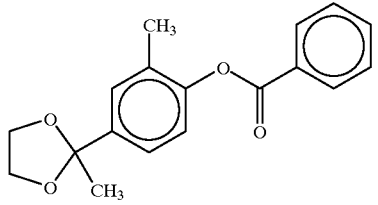

226 g of the compound of Example 3, 49 g of ethylene glycol and 6 g of methanesulfonic acid are stirred for 24 hours at room temperature (RT) in 1 liter of methylene chloride. The mixture is treated with 30% strength NaOCH₃ solution in methanol (pH=9) and concentrated, and the residue is taken up in tert-butyl methyl ether. The mixture is subsequently washed with NH₄Cl solution, 3× using saturated NaHCO₃ solution and 2× using water and reconcentrated. This gives 220 g of the title compound of an oil. IR (cm$^{-1}$)=1737, 1267, 1120, 709.

Example 5

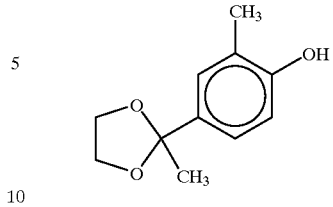

52 g of KOH in 25 g of water are added dropwise to 220 g of the compound of Example 4. After 1 hour, the mixture is concentrated, the residue is taken up in CH₂Cl₂/NH₄Cl solution, and the mixture is extracted 3× using water, dried and concentrated. 147 g of the title compound remain as an oil. IR (cm$^{-1}$)=1274, 1122, 1039, 819.

Example 6

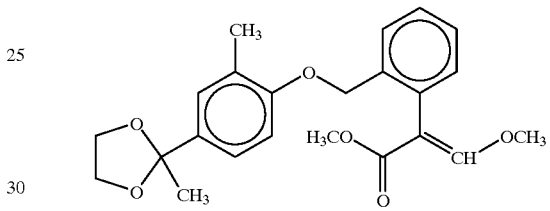

5 g of NaOCH₃ and 100 mg of potassium iodide are added to 4.9 g of the compound of Example 5 in 30 ml of dimethylformamide. After 1 hour, methyl α-(bromomethylphenyl)-β-methoxy-acrylate (for the preparation, cf. WO 94/05620) in 30 ml of DMF is added dropwise, and stirring is continued overnight at room temperature (RT). The mixture is subsequently taken up in CH₂Cl₂/water, extracted 3× using water, dried and concentrated. 9.7 g remain, and this is chromatographed over silica gel using toluene/acetone (5:1). This gives 1.5 g of the title compound as an oil. IR (cm$^{-3}$)=1709, 1632, 1258, 1131, 770.

TABLE

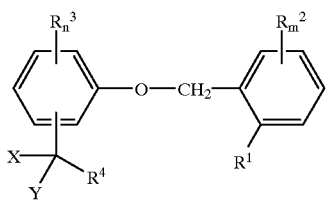

I

| No. | R$^1$ | R$^2_m$ | R$^3_n$ | # | R$^4$ | X | Y | Physical data* |
|---|---|---|---|---|---|---|---|---|
| 01 | C(NOCH₃)CONHCH₃ | — | 2-CH₃ | 4 | CH₃ | OCH₂CH₂O | | 94–97 |
| 02 | C(NOCH₃)CONHCH₃ | — | 3-CH₃ | 4 | CH₃ | OCH₂CH₂O | | 53–56 |
| 03 | C(NOCH₃)CONHCH₃ | — | 2,5-(CH₃)₂ | 4 | CH₃ | OCH₂CH₂O | | 141–143 |
| 04 | C(NOCH₃)CONHCH₃ | — | 2-CH₃ | 4 | CH₃ | OCH(CH₃)CH₂O | | 96–98 |
| 05 | C(NOCH₃)CONHCH₃ | — | 3-CH₃ | 4 | CH₃ | OCH(CH₃)CH₂O | | 84–86 |
| 06 | C(NOCH₃)CONHCH₃ | — | 2,5-(CH₃)₂ | 4 | CH₃ | OCH(CH₃)CH₂O | | 97–99 |

TABLE-continued

I

| No. | R$^1$ | R$^2_m$ | R$^3_n$ | # | R$^4$ | X | Y | Physical data* |
|---|---|---|---|---|---|---|---|---|
| 07 | C(NOCH$_3$)CONHCH$_3$ | — | 2-CH$_3$ | 4 | CH$_3$ | OCH(CH$_3$)CH(CH$_3$)O | | 80–83 |
| 08 | C(NOCH$_3$)CONHCH$_3$ | — | 3-CH$_3$ | 4 | CH$_3$ | OCH(CH$_3$)CH(CH$_3$)O | | 86–88 |
| 09 | C(NOCH$_3$)CONHCH$_3$ | — | 2,5-(CH$_3$)$_2$ | 4 | CH$_3$ | OCH(CH$_3$)CH(CH$_3$)O | | 118–120 |
| 10 | C(NOCH$_3$)CONHCH$_3$ | — | 2-CH$_3$ | 4 | CH$_3$ | OCH(CH$_2$CH$_3$)CH$_2$O | | 103–105 |
| 11 | C(NOCH$_3$)CONHCH$_3$ | — | 3-CH$_3$ | 4 | CH$_3$ | OCH(CH$_2$CH$_3$)CH$_2$O | | 73–75 |
| 12 | C(NOCH$_3$)CONHCH$_3$ | — | 2,5-(CH$_3$)$_2$ | 4 | CH$_3$ | OCH(CH$_2$CH$_3$)CH$_2$O | | 64–66 |
| 13 | C(NOCH$_3$)CONHCH$_3$ | — | 2-CH$_3$ | 4 | CH$_3$ | OCH[(CH$_2$)$_2$CH$_3$]CH$_2$O | | 85–87 |
| 14 | C(NOCH$_3$)CONHCH$_3$ | — | 3-CH$_3$ | 4 | CH$_3$ | OCH[(CH$_2$)$_2$CH$_3$]CH$_2$O | | 79–81 |
| 15 | C(NOCH$_3$)CONHCH$_3$ | — | 2,5-(CH$_3$)$_2$ | 4 | CH$_3$ | OCH[(CH$_2$)$_2$CH$_3$]CH$_2$O | | 60–62 |

Position of group CR$^4$XY
*m.p. (° C.);

Examples for the action against harmful fungi

The fungicidal action of the compounds of the general formula I was demonstrated by the following experiments:

The active ingredients were prepared as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols) and diluted with water to give the desired concentration.

Action against *Fusarium culmorum*

Leaves of wheat seedlings (cultivar "Kanzler") were first treated with the aqueous preparation of the active ingredients (rate of application: 250 ppm). After approximately 24 hours, the plants were treated with a spore suspension of the fungus *Fusarium culmorum*. The plants which had thus been treated were subsequently incubated for 6 days at 22–24° C. and a relative atmospheric humidity of >90%. The extent of fungal development was subsequently determined.

In this test, the disease level of the plants treated with compounds 01, 02 and 04 to 15 according to the invention was 15% and less, while the disease level of the untreated (control) plants was 60%.

Action against *Pyricularia oryzae* (rice blast)

Rice seedlings (cultivar: "Tai Nong 67") were sprayed to drip point with the preparation of active ingredient (rate of application: 63 ppm). After 24 hours, the plants were sprayed with an aqueous spore suspension of the fungus *Pyricularia oryzae* and kept for 6 days at 22–24° C. at a relative atmospheric humidity of 95–99%. Assessment was carried out visually.

In this test, the disease level of the plants treated with compounds 01 and 03 to 15 according to the invention was 15% and less, while the disease level of the untreated (control) plants was 75%.

Examples for the action against animal pests

The action of the compounds of the general formula I against animal pests was demonstrated by the following experiments:

The active ingredients were prepared
a. as an 0.1% strength solution in acetone or
b. as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols)

and diluted to give the desired concentration, using acetone in the case of a. and water in the case of b. After the experiments had been concluded, the lowest concentration was determined in each case at which the compounds still caused an 80 to 100% inhibition or mortality in comparison with untreated control experiments (limit or minimal concentration).

We claim:
1. A compound of the general formula I

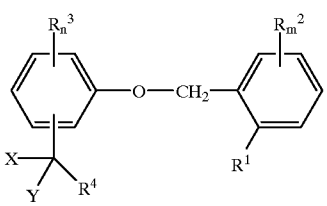

where the indices and the substituents have the following meanings:

R$^1$ is C(CO$_2$CH$_3$)=CHOCH$_3$, C(CO$_2$CH$_3$)=NOCH$_3$, C(CONHCH$_3$)=NOCH$_3$ and N(OCH$_3$)—CO$_2$CH$_3$;

R$^2$ is cyano, halogen, C$_1$–C$_4$-alkyl and C$_1$–C$_4$-alkoxy;

m is 0 or 1;

R$^3$ is cyano, halogen, C$_1$–C$_4$-alkyl, C$_1$–C$_4$-haloalkyl and C$_1$–C$_4$-alkoxy;

n is 0, 1, 2 or 3, it being possible for the substituents R$^3$ to be different from each other when n is 2 or 3;

R$^4$ is hydrogen, C$_1$–C$_4$-alkyl, C$_1$–C$_4$-haloalkyl, C$_3$–C$_6$-cycloalkyl and phenyl;

X and Y together with the C atom to which they are bonded form one of the following heterocycles XY.1, XY.3, XY.5 and XY.7

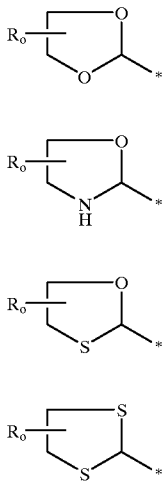

where the bond marked ● represents the bond to the phenyl ring and where o is 0, 1, 2 or 3, it being possible for the substituents R to be different from each other when o is 2 or 3; and R is $C_1$–$C_4$-alkyl, oxo(C=O), $C_3$–$C_6$cycloalkyl, $C_1$–$C_4$-alkoxycarbonyl, cyano, aryl and heteroaryl.

2. A process for the preparation of compounds I as defined in claim 1 where the groups X and Y together with the C atom to which they are bonded are an oxirane ring, which comprises reacting a carbonyl compound of the formula II

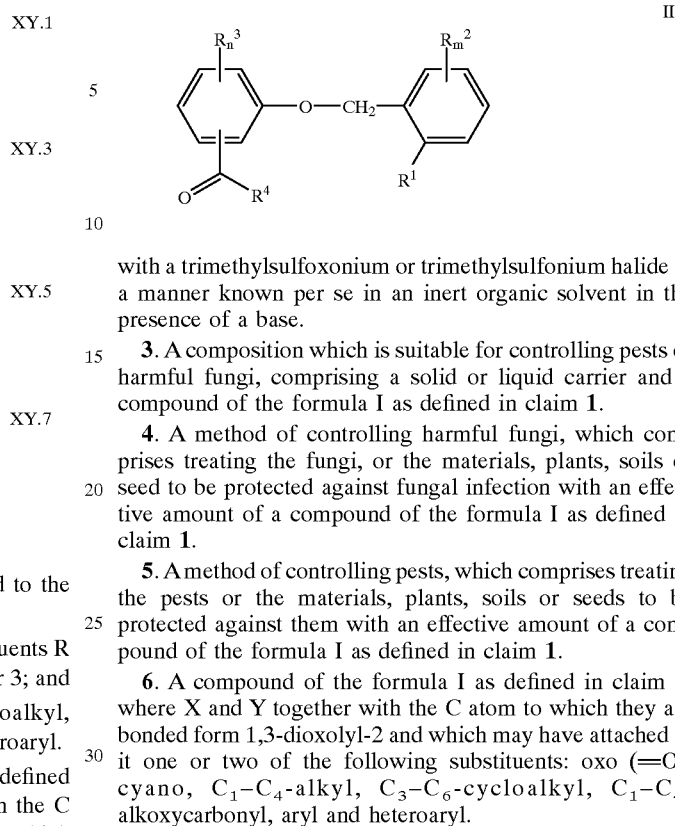

with a trimethylsulfoxonium or trimethylsulfonium halide in a manner known per se in an inert organic solvent in the presence of a base.

3. A composition which is suitable for controlling pests or harmful fungi, comprising a solid or liquid carrier and a compound of the formula I as defined in claim 1.

4. A method of controlling harmful fungi, which comprises treating the fungi, or the materials, plants, soils or seed to be protected against fungal infection with an effective amount of a compound of the formula I as defined in claim 1.

5. A method of controlling pests, which comprises treating the pests or the materials, plants, soils or seeds to be protected against them with an effective amount of a compound of the formula I as defined in claim 1.

6. A compound of the formula I as defined in claim 1, where X and Y together with the C atom to which they are bonded form 1,3-dioxolyl-2 and which may have attached to it one or two of the following substituents: oxo (=O), cyano, $C_1$–$C_4$-alkyl, $C_3$–$C_6$-cycloalkyl, $C_1$–$C_4$-alkoxycarbonyl, aryl and heteroaryl.

* * * * *

UNITED STATES PATENT AND TRADEMARK OFFICE
CERTIFICATE OF CORRECTION

PATENT NO.: 6,060,493

DATED: May 9, 2000

INVENTOR(S): SAUTER et al.

It is certified that error appears in the above-identified patent and that said Letters Patent is hereby corrected as shown below:

Col. 31, claim 1, line 24, "marked •" should be -- marked *--.

Signed and Sealed this

Twentieth Day of March, 2001

Attest:

NICHOLAS P. GODICI

*Attesting Officer*          *Acting Director of the United States Patent and Trademark Office*